United States Patent
Ralph et al.

(10) Patent No.: US 11,564,655 B2
(45) Date of Patent: Jan. 31, 2023

(54) REAL-TIME SAMPLING DEVICE

(71) Applicant: OLYMPUS MEDICAL SYSTEMS CORPORATION, Hachioji (JP)

(72) Inventors: Christopher R. Ralph, Woodinville, WA (US); Jason T. Panzenbeck, Seattle, WA (US)

(73) Assignee: OLYMPUS MEDICAL SYSTEMS CORPORATION, Tokyo (JP)

( * ) Notice: Subject to any disclaimer, the term of this patent is extended or adjusted under 35 U.S.C. 154(b) by 380 days.

(21) Appl. No.: 16/912,014

(22) Filed: Jun. 25, 2020

(65) Prior Publication Data
US 2021/0000334 A1      Jan. 7, 2021

Related U.S. Application Data

(60) Provisional application No. 62/870,545, filed on Jul. 3, 2019.

(51) Int. Cl.
*A61B 1/00*       (2006.01)
*A61B 8/00*       (2006.01)
(Continued)

(52) U.S. Cl.
CPC ............ *A61B 8/445* (2013.01); *A61B 1/0011* (2013.01); *A61B 1/00087* (2013.01); *A61B 1/00098* (2013.01); *A61B 1/00112* (2013.01); *A61B 1/00135* (2013.01); *A61B 1/00137* (2013.01); *A61B 1/00154* (2013.01);
(Continued)

(58) Field of Classification Search
CPC ............ A61B 1/00098; A61B 1/00135; A61B 1/00137; A61B 1/2676; A61B 1/00; A61M 25/007; A61M 2025/004; A61M 25/0026
See application file for complete search history.

(56) References Cited

U.S. PATENT DOCUMENTS 5,704,361 A      1/1998   Seward et al.
2014/0296708 A1  10/2014  Flaherty et al.
(Continued)

FOREIGN PATENT DOCUMENTS

DE      102020117387       1/2021
EP         266415 A2       11/2013
(Continued)

OTHER PUBLICATIONS

Dec. 21, 2020, Search Report for International App No. GB2010139.0.

*Primary Examiner* — Deanna K Hall
(74) *Attorney, Agent, or Firm* — Schwegman Lundberg & Woessner, P.A.

(57) ABSTRACT

An elongated access device used in a medical system. The elongated access device slidably receives a medical tool and an ultrasound probe. The elongated access device includes a sheath and an intraluminal tip attached to the distal end of the sheath. The intraluminal tip includes ramp and nose donuts being spaced apart from one another and configured to be attached to one or more elongated sleeves. One or more orientation pins are engaged with the respective ramp and nose donuts and may be anchored within the sheath. The medical tool is engaged with a ramp formed in the ramp donut or a ramp received within the ramp donut. The ultrasound probe is configured to engage with the intraluminal tip so as to ensure that the medical tool directionality is oriented toward a target during a procedure.

19 Claims, 13 Drawing Sheets

(51) Int. Cl.
   *A61B 8/12*      (2006.01)
   *A61B 1/018*     (2006.01)
   *A61B 1/267*     (2006.01)
   *A61M 25/00*     (2006.01)
   *A61M 25/06*     (2006.01)
   *A61B 10/04*     (2006.01)
   *A61B 17/34*     (2006.01)

(52) U.S. Cl.
   CPC ............ *A61B 1/018* (2013.01); *A61B 1/2676* (2013.01); *A61B 8/12* (2013.01); *A61M 25/0069* (2013.01); *A61B 8/4281* (2013.01); *A61B 2010/045* (2013.01); *A61B 2017/3413* (2013.01); *A61M 25/007* (2013.01); *A61M 25/0026* (2013.01); *A61M 25/0045* (2013.01); *A61M 25/0068* (2013.01); *A61M 25/0097* (2013.01); *A61M 25/0662* (2013.01)

(56)           References Cited

U.S. PATENT DOCUMENTS

2018/0153530 A1    6/2018   Johnson et al.
2021/0000332 A1    1/2021   Ralph et al.

FOREIGN PATENT DOCUMENTS

EP            2865345 A1    4/2015
GB            2587873       4/2021
JP            2021010736    2/2021

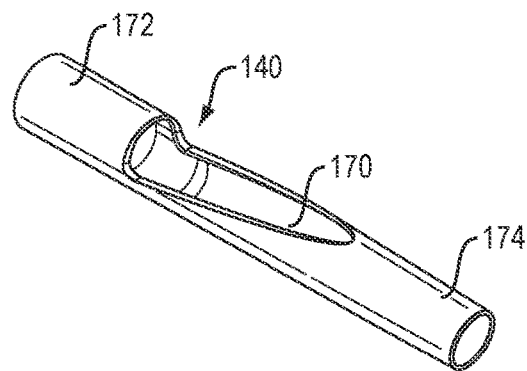
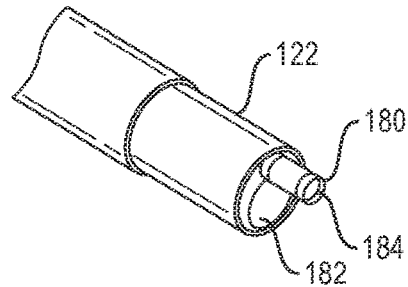
FIG. 14    FIG. 15
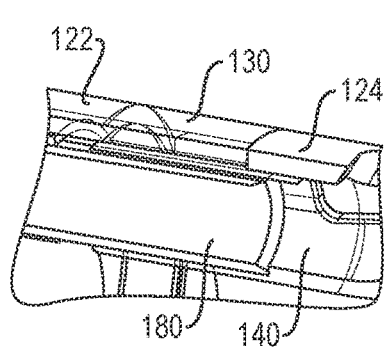
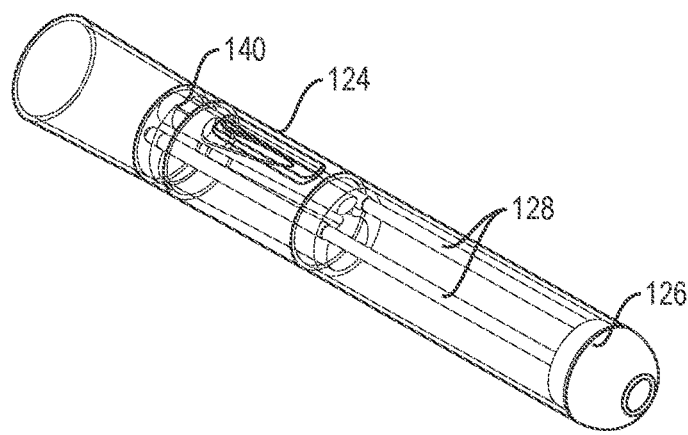
FIG. 16    FIG. 17

REAL-TIME SAMPLING DEVICE

CROSS REFERENCE TO RELATED APPLICATIONS

This application claims priority to U.S. Provisional Application No. 62/870,545 filed on Jul. 3, 2019, which is hereby fully incorporated by reference.

DESCRIPTION OF THE RELATED ART

The medical devices that are currently available for the ultrasound visualization and sampling of peripheral lung tumors are limited in their range of motion and diagnostic capabilities. Typically, during peripheral sampling a guide sheath is fed through a bronchoscope and extended so far beyond the reach of the bronchoscope that the distal end of the guide sheath is not visible. A radial endobronchial ultrasound (EBUS) miniprobe is passed through the guide sheath and is used to determine the approximate location of the tumor.

Unfortunately, a peripheral tumor that is located off to one side of an airway, as opposed to one that is centered around an airway, has a substantially lower diagnostic yield in part due to the limitations of current radial EBUS technology, which allows the operator to discern the depth from the probe, but not the direction of the tumor or lesion. A sampling needle must extend off-axis from the sheath and, therefore, requires a knowledge of rotational orientation of the needle and the target. The radial ultrasound probe does not show the orientation of the needle to the lesion. The radial ultrasound image is a 360° image that allows the user to see a lesion, however, the user cannot tell if the needle is pointing towards the lesion.

BRIEF SUMMARY OF EMBODIMENTS

Embodiments of the technology disclosed herein are directed to a flexible device for allowing real-time viewing of a tissue sampling or drug delivery procedure in a patient beyond the viewing range of an endoscope that may be used to transport the device.

Accordingly, one aspect of the disclosed technology is directed an elongated access device having respective proximal and distal ends and being used in a medical system. The elongated access device receives a medical tool and an ultrasound probe in separate lumen. The elongated access device includes a sheath and an intraluminal tip attached to the sheath. The intraluminal tip includes a hub and a nose device being spaced apart from one another to form an ultrasound probe cavity formed by an oversleeve. One or more orientation pins engages with the hub and nose device and may be anchored within the sheath. A ramp device is received within the hub. The medical tool is configured to deflect off-axis when engaged with the ramp device. The ultrasound probe is received within the ultrasound probe cavity of the intraluminal tip so as to ensure that the deflected medical tool is oriented toward a target during a medical procedure based on proximity to image anomalies related to the one or more pins.

Other features and aspects of the disclosed technology will become apparent from the following detailed description, taken in conjunction with the accompanying drawings, which illustrate, by way of example, the features in accordance with embodiments of the disclosed technology. The summary is not intended to limit the scope of any inventions described herein, which are defined solely by the claims attached hereto.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

FIG. 14 is an isometric view of a component of the device shown in FIG. 10.

FIG. 15 is an isometric view of a distal end of a sheath that forms part of the device shown in FIG. 10.

FIG. 16 is a cross-sectional view of a portion of the distal end of the elongated access device shown in FIG. 10.

FIG. 17 is an x-ray view of the distal end of the elongated access device shown in FIG. 10.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

Figure 1:
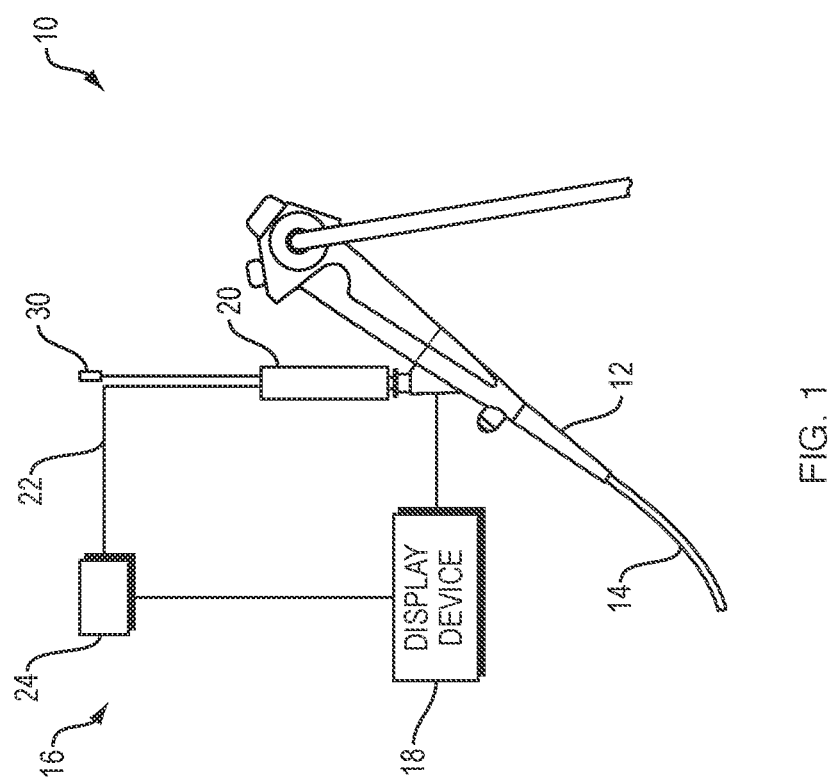
FIG. 1 illustrates an example of an elongated access device used in a bronchoscope system in accordance with one embodiment of the disclosed technology.

Referring now to FIG. 1, a bronchoscope system 10 includes a bronchoscope 12 with an insertion tube 14, a radial ultrasound system 16 and an elongated access device 20. The radial ultrasound system 16 includes a signal processor 24, a display device 18 and a radial ultrasound probe 22. The radial ultrasound probe 22 and a medical device 30, such as a needle for tissue sampling and/or medicate delivery, are received within the bronchoscope 12 via a handle component of the elongated access device 20.

The display device 18 is in wired or wireless signal communication with the bronchoscope 12 and/or the signal processor 24. The display device 18 presents images based on information received from the bronchoscope 12 and/or the signal processor 24 that receives image information from a radial ultrasound transducer at the distal end of the radial ultrasound probe 22. A diagnostic bronchoscope (e.g., BF-X190 produced by Olympus®) is an example of the bronchoscope 12 and the radial endobronchial ultrasound (EBUS) miniprobes produced by Olympus® are examples of the radial ultrasound system 16.

Figure 2:
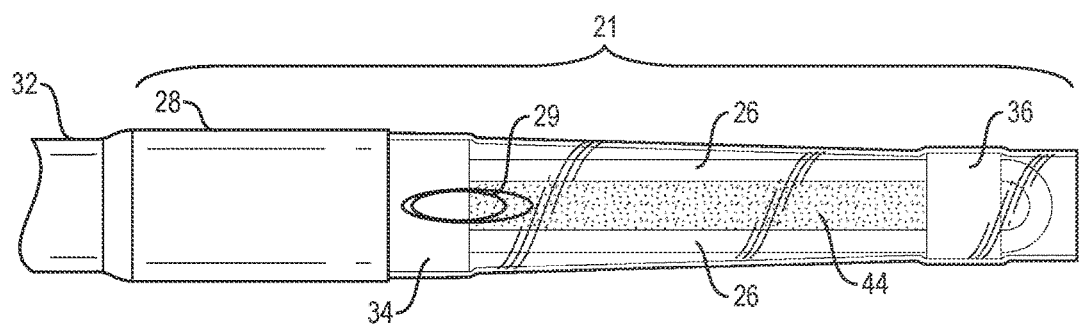
FIG. 2 is a top view of a distal end of the elongated access device in accordance with one embodiment of the disclosed technology.
Figure 3:
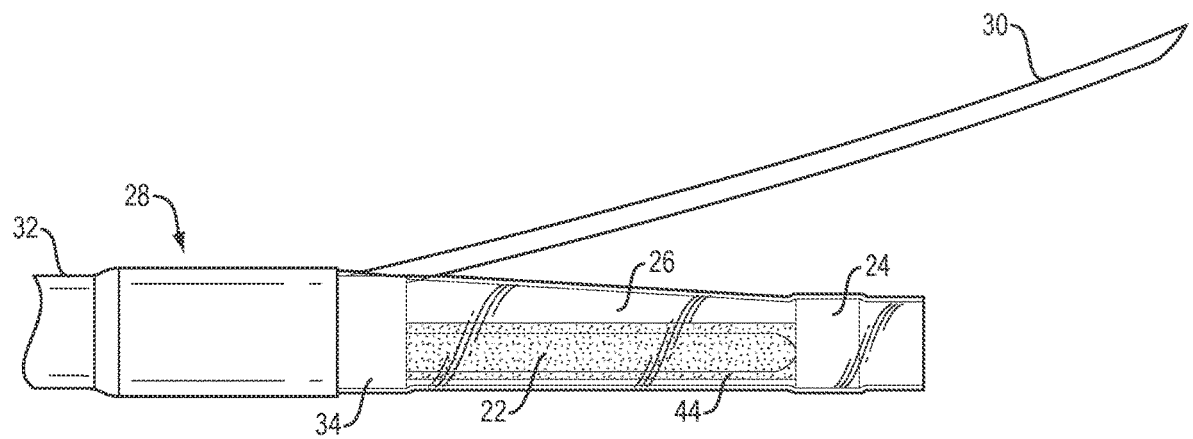
FIG. 3 is a side view of the distal end of the elongated access device of FIG. 2.
Figure 7:
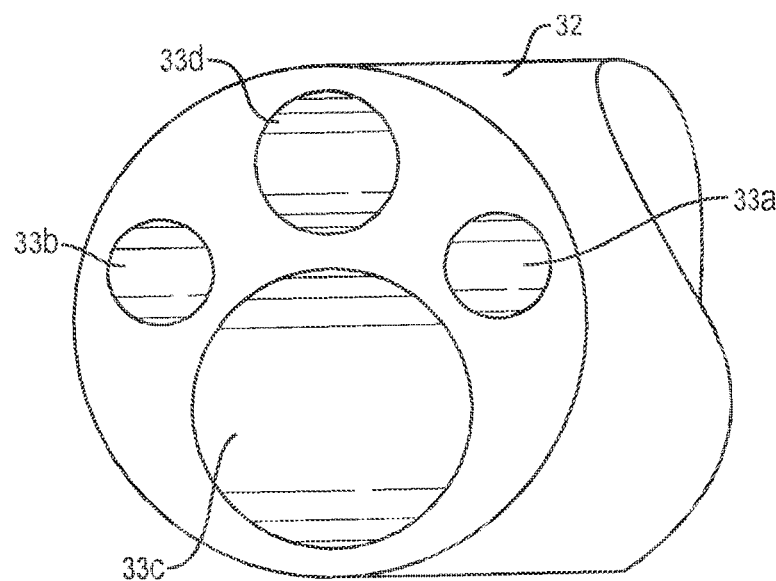
FIG. 7 illustrates a portion of an exemplary sheath of the elongated access device.

FIG. 2 is a top view and FIG. 3 is a side view of a distal end of the elongated access device 20 in accordance with one embodiment of the disclosed technology. The medical device 30 and the ultrasound probe 22 are slidably received within the elongated access device 20. The elongated access device 20 includes a sheath 32 and an intraluminal tip 21 configured to be attached to one another at a distal end of the sheath 32. The sheath 32 includes a plurality of lumens, for example, four lumens 33a, 33b, 33c, and 33d each of which receives various components therethrough as best depicted in FIG. 7 and described below. The intraluminal tip 21 includes ramp and nose donuts 34, 36 that are spaced apart from one another and are configured to be positioned within a sleeve 28. The sleeve 28 includes an exit opening/port 29 that allows the medical device 30 to protrude therefrom as depicted in FIG. 3. The sleeve 28 defines an ultrasound transparent window between the donuts 34, 36 that encompass the ultrasound probe 22. An ultrasound gel 44 or other suitable fluid such as, for example, isotonic saline, is inserted into the tip 21 to ensure continuous and reliable propagation of ultrasound energy. The sleeve 28 is made of commercially available ultrasound transparent material such as Pebax® which is a thermoplastic elastomer made of flexible polyether and the highest rigid polyamide component of the commercial grades providing for maximum mechanical performance in various molded components used in medical devices.

Figure 4:
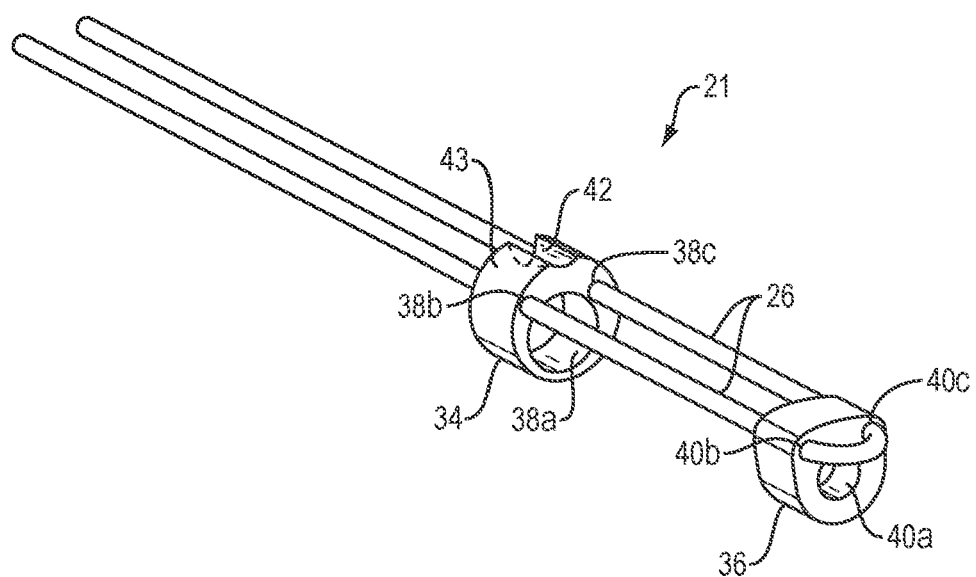
FIG. 4 is an isometric view of the distal end of the elongated access device when both sheath and the elongated sleeve are removed to illustrate the manner in which the orientation pins and the respective ramp and nose donuts engaged with one another.

FIG. 4 is an isometric view of a portion of one embodiment of the tip 21 with the sleeve 28 removed in order to illustrate the manner in which orientation pins 26 and the ramp and nose donuts 34, 36 are engaged with one another. The ramp donut 34 is generally cylindrical in shape having a first plurality of passages 38a, 38b, and 38c formed thereto to permit the ultrasound probe 22 and the orientation pins 26 to pass therethrough. The ramp donut 34 includes a ramped groove 42 formed on an outer surface 43. The ramped groove 42 is angled to deflect the medical device 30 away from a longitudinal axis of the intraluminal tip 21 when the medical device 30 is engaged with the ramp donut 34 during a medical procedure. The ramped groove 42 has a central axis that diverges from a longitudinal axis of the intraluminal tip 21 and the sheath 32. The ramped groove 42 enables repeated eccentric sampling with a needle for example without wearing down the ramped groove 42. The ramp and nose donuts 34 and 36 may be made of stainless steel, polyphenylsulfone (PPSU) or comparable materials. In one embodiment, the passage 38a is used to receive the ultrasound probe 22 and the respective passages 38b, 38c are used for the orientation pins 26 to pass therethrough.

The nose donut 36 is generally cylindrical in shape having a plurality of passages 40a, 40b, and 40c. In one embodiment, the passage 40a is used to receive the ultrasound gel 44 to flow therein and provide a bottoming out point for insertion of the ultrasound probe 22, which plugs up the passage 40a so as to prevent the ultrasound gel 44 (e.g., FIGS. 2 & 3) from escaping back out. The passages 40b, 40c attach to the orientation pins 26. In one embodiment, the orientation pins 26 may be formed from one continuous pin material that is formed into a U-shape, as depicted in FIGS. 2-4.

The orientation pins 26 may be made of nitinol, stainless steel, a stainless steel braid or comparable material having ultrasound reflective properties. The orientation pins 26 may have echogenic properties for reflecting ultrasound signals transmitted from the ultrasound probe and thus provide a shadowing effect that resembles "headlights" in the ultrasound image. The headlight effect indicates where the medical device 30 will exit the ramped groove 42. The orientation pins 26 may include reflective features, such as etchings or grooves, for increasing the echogenicity of the pins 26. As noted hereinbefore, the orientation pins 26 are flexible and return to their original shape after being bent. The orientation pins 26 may be anchored within the sheath 32 to help hold the ramp and nose donuts 34, 36 in place. The orientation pins 26 may have a variety of shapes, such as round, oval, rectangular, with the plurality of passages having comparable shapes.

Figure 5:
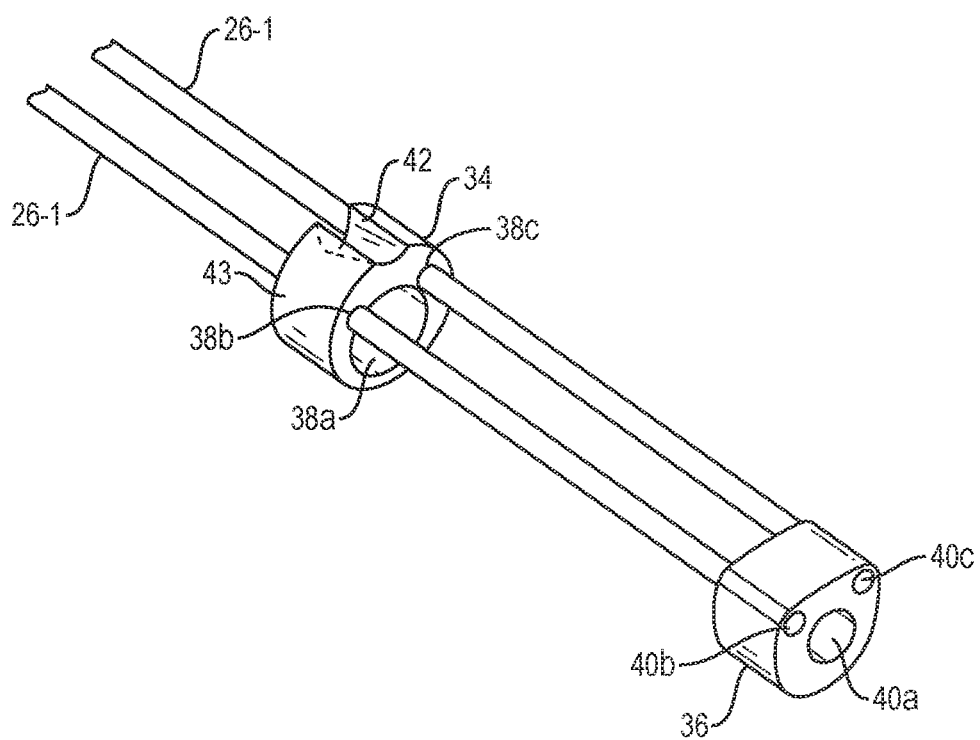
FIG. 5 illustrates an embodiment of the orientation pins and the respective ramp and nose donuts engaged with one another.

FIG. 5 is similar to FIG. 4 except the pins 26-1 are two separate pins.

Figure 6:
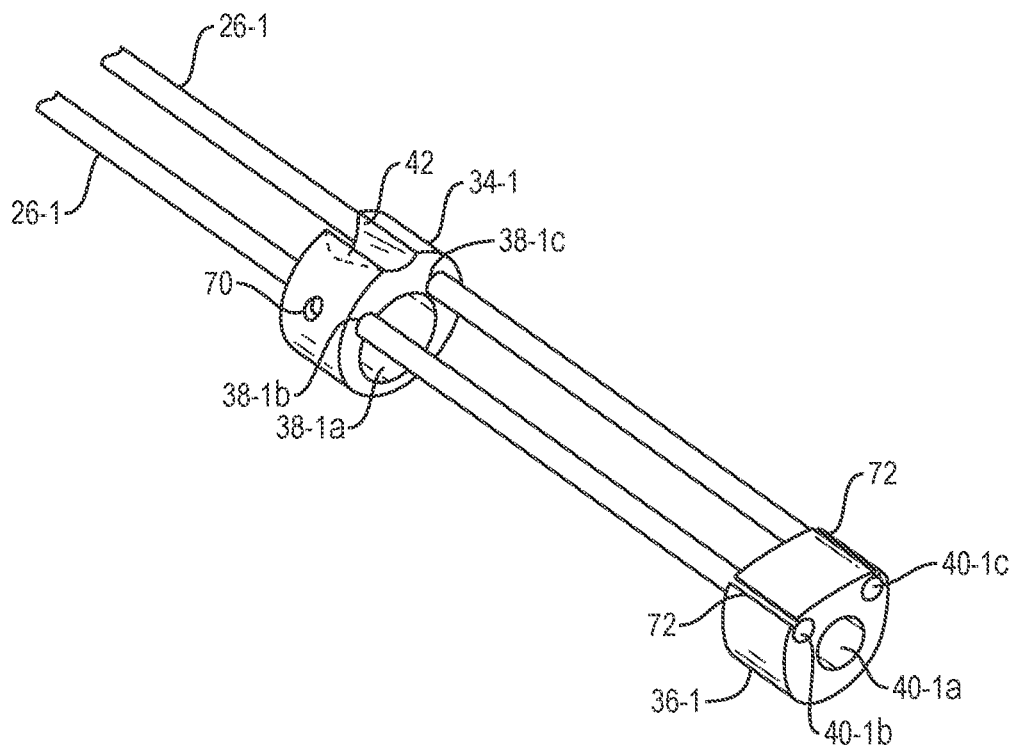
FIG. 6 illustrates an embodiment of the orientation pins and the respective ramp and nose donuts engaged with one another.

FIG. 6 is similar to FIG. 5 except ramp and nose donuts 34-1, 36-1 have different configurations. The nose donut 36-1 includes one or more slits 72 along pin passages 40-1b, 40-1c. The slits 72 can be crimped after each of the orientation pins 26-1 is inserted into the respective passages 40-1b, 40-1c. The crimping or peening process is performed in order to apply a force between the nose donut 36-1 and the orientation pins 26-1. In one embodiment, after the orientation pins 26-1 are inserted into the plurality of passages to predefined positions, a cryogenic press-fit action is performed to cause the ramp and nose donuts 34-1, 36-1 to apply a securing force. In one embodiment, laser spot welds may be applied between the pins 26-1 and the ramp donut 34-1 through a cavity 70 and/or the nose donut 36-1 via the slits 72.

FIG. 7 illustrates a portion of the sheath 32 that is attached to the intraluminal tip 21. As noted previously, the sheath 32 includes a plurality of lumens, for example, four lumens 33a, 33b, 33c, and 33d each of which receives various components such as the medical device 30, the orientation pins 26, and the ultrasonic probe 22. For example, each of the orientation pins 26 are secured within the lumens 33a, 33b and the ultrasonic probe 22 slidably passes through lumen 33c. The medical device 30 slidably passes through the lumen 33d. The sheath 32 extends from a handle portion (not shown). The lumens 33a, 33b, 33c, and 33d are all accessible via a distal face of the sheath 32. The lumens 33c, 33d extend to proximal ports (not shown) located at the handle portion, a port on a handle of the bronchoscope or other scope device, or at a position accessible by an operator or a medical professional. The lumens 33c, 33d allow devices to be inserted from the proximal end all the way to the distal end of the sheath 32. As noted hereinbefore, the radial probe (i.e., ultrasound) lumen 33c is sized to slidably receive the radial ultrasound probe 22 as seen best in FIG. 8. The sheath 32 is made of flexible materials such as a braided (stainless steel) sheath with PTFE liners in the lumens and thermoplastic elastomer materials (e.g., Pebax® material) making up the sheath body and the outer jacket. The sheath 32 and the intraluminal tip 21 are bonded to one another via the orientation pins 26 and/or the sleeve 28 made of thermoplastic elastomer material such as Pebax® that provides a strong bonding mechanism.

Figure 8:
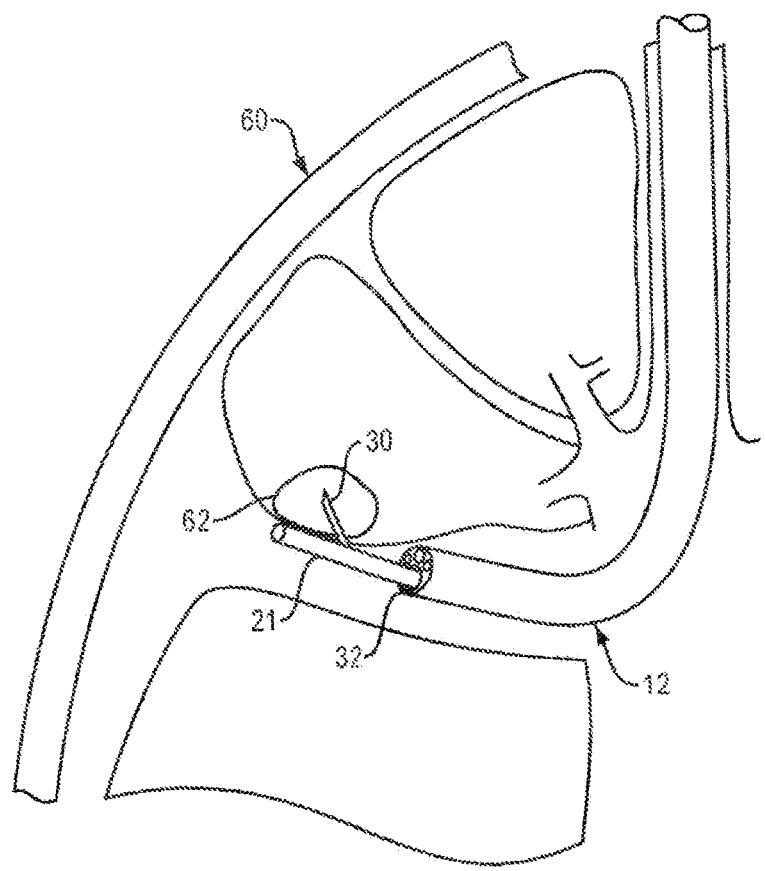
FIG. 8 illustrates an example of a pulmonary portion of a body in which the distal end of the elongated access device and a bronchoscope are engaged in sampling of a peripheral tumor that is located off to one side of an airway.
Figure 9:
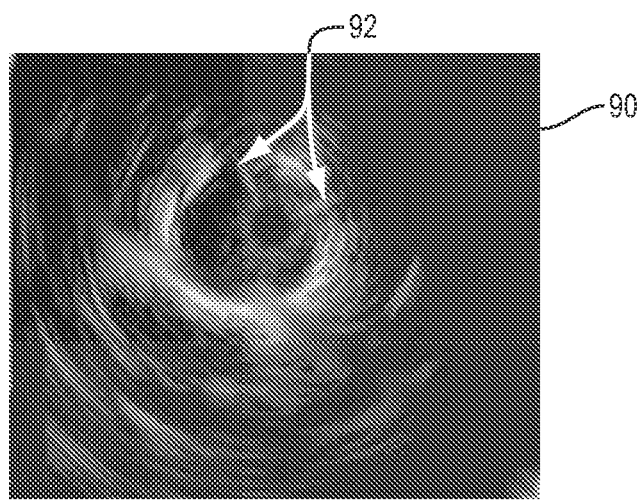
FIG. 9 is an exemplary image generated by a radial ultrasound probe used with the components shown in FIGS. 1-8.
Figure 10:
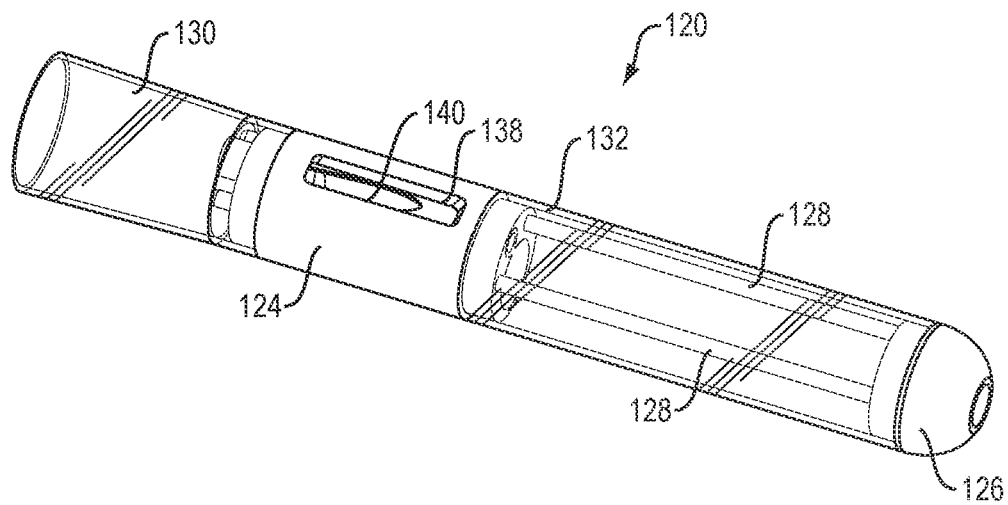
FIG. 10 is an isometric view of the distal end of the elongated access device formed in accordance with one embodiment of the technology described herein.
Figure 11:
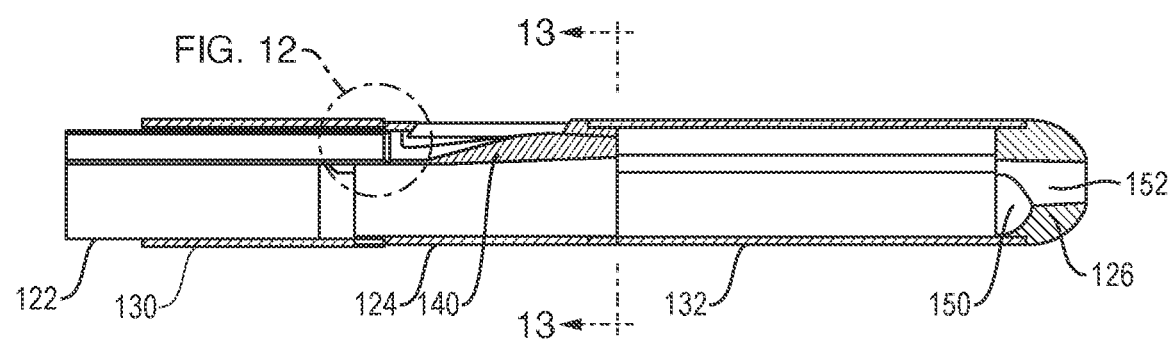
FIG. 11 is a cross-sectional view of the device shown in FIG. 10.
Figure 12:
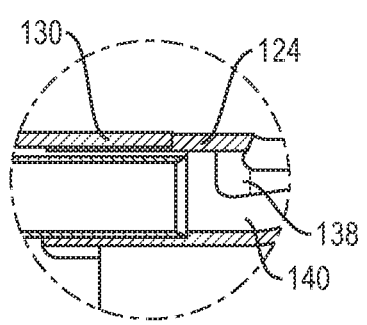
FIG. 12 is a zoomed-in view of a portion of the device shown in FIG. 11.
Figure 13:
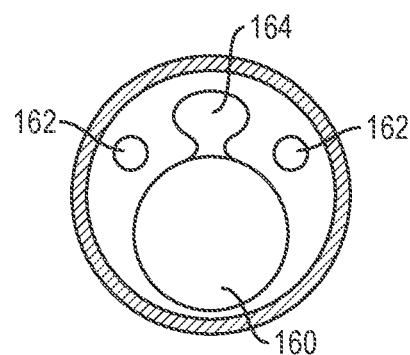
FIG. 13 is a cross-sectional view of the device shown in FIG. 10.

FIG. 8 illustrates an example of a portion of pulmonary body 60 in which the distal end of the elongated access device 20 and the bronchoscope 12 are engaged in sampling of a bio-tissue target or a peripheral tumor 62 that is located off to one side of an airway. FIG. 9 is an exemplary image generated by the radial ultrasound probe 22 used with the components shown in FIGS. 1-8. The distal end of the elongated access device 20 is flexible and capable of moving through the articulated bronchoscope 12. As noted previously, the sleeve 28 creates an ultrasound window that encompass the ultrasound probe 22 surrounded by the ultrasound gel 44 so that during a procedure, when the ultrasound window of the tip 21 is in contact with the bio-tissue target 62 or airway wall with no air gap therebetween, an ultrasound signal is transmitted directly into the target 62. It should be noted that the orientation pins 26 are visible on the ultrasound image 90 during the procedure and are used to ensure that the medical device 30 protrudes from the sheath 32 at an exact position with respect to the bio-tissue target 62 for biopsy.

When the radial ultrasound probe 22 is positioned within the tip 21, the radial ultrasound probe 22 is able to produce a 360° image. The 360° image includes reflections of the orientation pins 26. Because the orientation pins 26 are located on the same half of the first lumen 33c, then any medical device 30 passed through the second lumen 33d will interact with the target 62 visually located on the 360° image between the shortest arced distance between the reflections of the orientation pins 26 as seen best in FIG. 9. As noted hereinbefore, the disclosed technology uses echogenic orientation pins 26 that are visible on the ultrasound image and thus alert the user to the rotational orientation of the distal end of the access device 20 and the medical device 30 relative to the target 62. Moreover, one advantage of the disclosed technology is that during the operation, when the ultrasound window is in contact with the target 62 or airway wall with no air gap therebetween, an ultrasound signal is transmitted directly into the target 62.

Continue referring to FIG. 8, in operation and by non-limiting example, the bronchoscope 12 is advanced through the trachea of a patient or other examinee and into a bronchial passage near the target 62. The elongated access device 20 (e.g., the sheath 32 and the intraluminal tip 21) of FIG. 2 is advanced through one of the lumens of the bronchoscope 12 and distally beyond the bronchoscope 12 to provide an ultrasound image of the bronchial airway. As the intraluminal tip 21 approaches the target 62, the ultrasound probe 22 provides an ultrasound image of the eccentric target 62 as seen best in FIG. 9. With the ultrasound probe 22 positioned in ultrasound contact with the eccentric the target 62, the user or the medical professional orients the tip 21 so that the viewed image shows the feedback associated with the bio-tissue target 62 is located within the echo shadows produced by reflections of the ultrasound signals of the pins 26, then distally advances the medical device 30 through the passage 31d. As noted, the ultrasound probe 22 is configured to engage with the intraluminal tip 21 so as to ensure that the medical device 30 directionality is oriented directly toward a bio-tissue target during the operation. Finally, after the biopsy or other procedure is completed, the medical device 30 is then retracted into the sheath 32 and the distal end of the elongated access device 20 proximally retracted into the bronchoscope 12 and removed from the patient.

Referring back to FIG. 9, which illustrates the image 90 outputted to the display device 18. The image 90 is generated by the radial ultrasound system 16 (FIG. 1) when the insertion tube 14 with an ultrasound transducer received at the distal end are positioned within a body lumen such as pulmonary body 60 depicted in FIG. 8. The image 90 shows an image with 360° of imaging features. The image 90 also includes feedback 92 identifying the orientation pins 26. The passage 33d is located between the orientation pins 26 where the arc between the pins feedback 92 is the smallest. Thus, an operator or user who is generally a medical professional will know that any medical device 30 exiting the passage 33d and the ramp 42 will always exit at about this smallest arc location. In the image 90, the medical device 30 will exit the tip 21 between approximate angular values 350° to 080°. In the image 90, 000° would be at the 12 o'clock position. Therefore, if a target is identified in a radial ultrasound image, all the user needs to do in order to have the medical device interact with that target 62 is to rotate the sheath 32 via a handle until the target 62 is located within a smallest pie of the 360° image that is bordered by the orientation pins feedback 92.

Moreover, in one embodiment, the disclosed technology is directed to a method of making the intraluminal tip 21 attached to the sheath 32. The method includes forming the ramp and nose donuts 34, 36 each of which having respective first and second plurality of passages 38a, 38b, 38c and 40a, 40b, and 40c by molding, machining or printing. Next, inserting the orientation pins 26 through the respective second plurality of passages 38a, 38b, 38c and 40a, 40b, and 40c. Then attaching the pins 26 to the donuts 34, 36. Using a mandrel (not shown), creating the sleeve 28 by forming thermoplastic elastomer material over the respective ramp and nose donuts 34, 36, the orientation pins 26 and at least a portion of the mandrel. The formed thermoplastic elastomer material may be thermally reflowed over a portion of the sheath 32 thus bonding the tip 21 to the sheath 32. Other bonding methods may be used, such as adhering the pins 26 within respective lumen in the sheath 32. Next, inserting the ultrasound probe 22 through one of the first plurality of passage 38a of the ramp donut 34 and injecting the ultrasound gel 44 through one of the second plurality of passages 40a of the nose donut 36 and providing a bottoming out point for the inserted ultrasound probe 22, which plugs up the one of the second plurality of passages of the nose donut 36 so as to prevent the ultrasound gel 44 from escaping back out.

FIGS. 10-17 show an alternate distal tip 120. The distal tip 120 is attached to the distal end of a sheath 122 by an oversleeve 130. The distal tip 120 includes a distal cap 126 that allows for inserting an ultrasound gel into an ultrasound probe cavity. The distal tip 120 includes a proximal hub 124 for receiving an ultrasound probe and allowing it to pass into the ultrasound probe cavity. The distal tip 120 also includes orientation pins 128 that connect to the distal cap 126 and the hub 124 and may be received/connected to lumen within the sheath 122. The orientation pins 128 may be adhered (e.g., epoxy), insert molded and/or pressure fitted to the hub 124, the cap 126 and/or the sheath 122.

The cap 126 has a rounded distal surface for atraumatic tissue interaction. A lumen 152 extends from the rounded distal surface to a proximal surface. The lumen 152 is a port for receiving ultrasound gel from an insertion device (e.g., syringe). The cap 126 also includes a rounded internal surface on its proximal side, which is sized to allow docking of a distal end of the ultrasound probe.

The hub 124 includes two lumen 162 for receiving the orientation pins 128, an ultrasound probe passage 160, a ramp locking lumen 164 and a ramp lumen 138 that connects to the ramp locking lumen 164. A tool exit port is located at a side of the hub 124 at the ramp lumen 138. The hub 124 and the cap 126 may be a molded plastic or comparable material.

As shown in FIGS. 14-17, a ramp device 140 is received within the ramp lumen 138 and the locking lumen 164. As shown in FIG. 14, the ramp device 140 includes a distal section 174, a ramp section 170 and a proximal section 172. The distal section 174 has an oval cross-section. The locking lumen 164 has an oval cross-sectional configuration that corresponds to the configuration of the distal section 174. Thus, the distal section 174 when seated within the ramp locking lumen 164 limits rotation of the distal section 174 within the ramp locking lumen 164, thus keeping the ramp section 170 properly aligned within the hub 124. Other shapes for the locking components may be used to provide this anti-rotation feature.

The ramp device 140 is positioned longitudinally within the hub 124 in the ramp lumen 138 so that a distal edge around the ramp section 170 is positioned at or proximal of a distal edge of the tool exit port of the hub 124 and a proximal edge around the ramp section 170 is positioned at or proximal of a proximal edge of the tool exit port. The proximal and/or distal edges of the tool exit port may be angled (i.e., not perpendicular to a longitudinal axis of the hub 124) in order to facilitate easier exit of the tool, such as a sampling needle. The ramp device 140 may be made of a molded/machined metal or plastic.

As shown in FIGS. 15-17, the sheath 122 includes a probe lumen 182 and a tool lumen 184. A tool liner 180 surrounds the tool lumen 184. The tool liner 180 extends beyond the distal surface of the sheath 122. The proximal section 172 of the ramp device 140 has an inner diameter that is the same as or larger than the outer diameter of the tool liner 180. The tool liner 180 is received by the proximal section 172 of the ramp device 140 and is secured thereto by one of a pressure/snap fit, adhesive or some other means.

In one embodiment, an oversleeve material (e.g., Pebax®) 130 is applied (i.e., thermal reflowed via a heat source (e.g. laser)) over a proximal relief/flange portion of the hub 124 and a distal relief/flange section of the sheath 122. In one embodiment, a gap is included between the distal end of the sheath 122 and the proximal end of the hub 124. This allows for increased flexibility between the tip 120 and the sheath 122. A distal oversleeve or ultrasound window 132 is applied, in a similar manner as the oversleeve 130, over the orientation pins 128, a proximal relief/flange section of the distal tip 126 and a distal relief/flange section of the hub 124. The oversleeves 130, 132 may be adhered and/or thermal reflow bonded to the relief/flange sections. The orientation pins 128 may extend proximally from the hub 124 and into receiving cavities within the sheath 122 in order to provide greater stiffness between the components.

Figure 18:
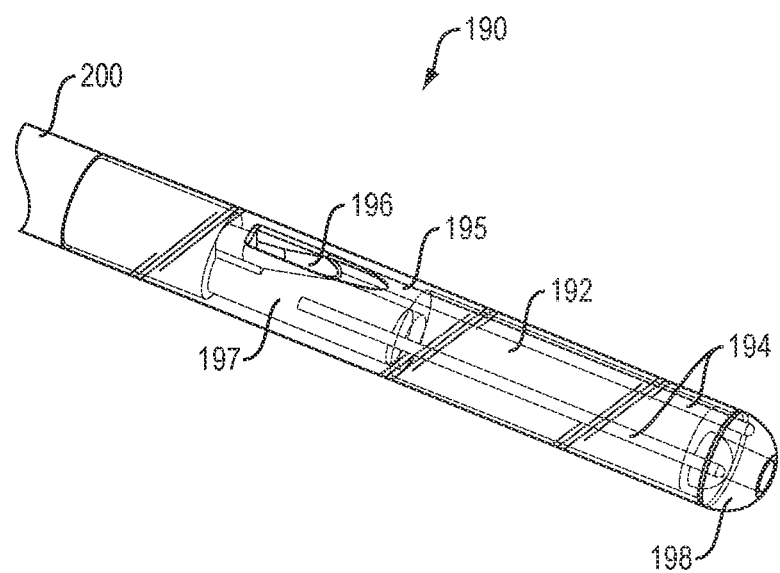
FIG. 18 is an isometric view of the distal end of the elongated access device formed in accordance with one embodiment of the technology described herein.

As shown in FIG. 18, unlike the embodiment shown in FIGS. 10-17, a distal tip 198 and a proximal hub 195 are primarily formed by a injection molded material 192 that encases orientation pins 194, a ramp 196 that extends from a tool lumen (i.e., needle liner) of a sheath 200 and a probe (i.e., ultrasound) lumen 197 that extends from an probe lumen of the sheath 200. The ramp 196 may be formed from or of the distal end of the needle liner. The reflowed material 192 is molded/formed to create support for the orientation pins 194, the ultrasound liner 197 and the ramp 196. The reflowed material 192 also forms a distal cap 198 similar in shape to the cap 126 of FIG. 10.

Figure 19:
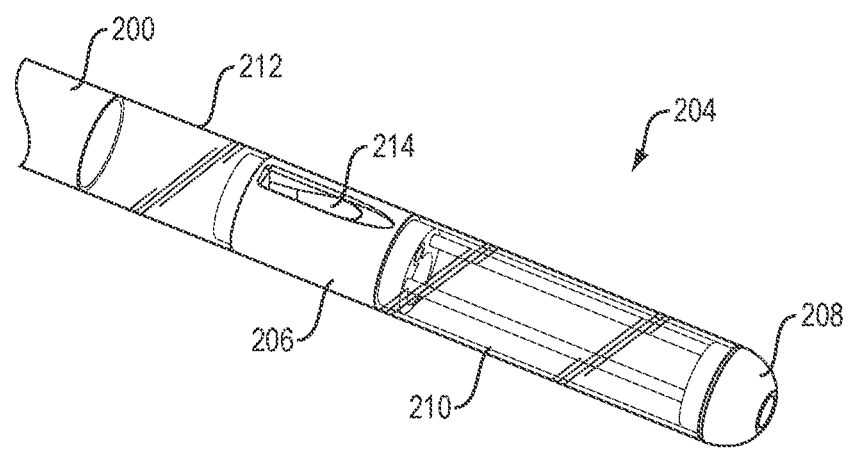
FIG. 19 is an isometric view of the distal end of the elongated access device formed in accordance with one embodiment of the technology described herein.

As shown in FIG. 19, a distal tip 204 includes a hub 206 and a distal cap 208 partially surrounded by a first thermal reflowed material 210 between the hub 206 and the cap 208 and a second thermal reflowed material 212 between the hub 206 and the sheath 200. The hub 206 supports a ramp 214 that extends from a tool lumen of the sheath 200. The hub 206 may also support a liner extending from the probe lumen of the sheath 200. Pins connect between the hub 206 and the cap 208 and are surrounded by the material 210. The hub 206 and/or the cap 208 are insert molded into the oversleeve materials 210, 212.

Figure 20:
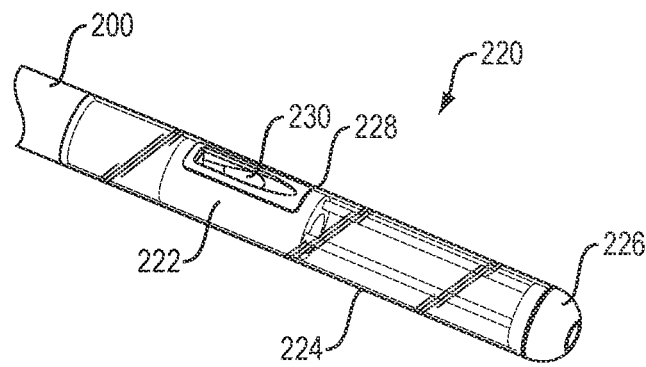
FIG. 20 is an isometric view of the distal end of the elongated access device formed in accordance with one embodiment of the technology described herein.

As shown in FIG. 20, a distal tip 220 is similar to the distal tip 204 shown in FIG. 19 except that an outer diameter of a hub 222 has been reduced in order to allow for a single thermal reflowed material 224 to extend from a distal cap 226 over the hub 222 to the sheath 200. An edge 228 surrounds the exit port. The edge 228 has a larger radius from a centerline of the hub 222 than the rest of the hub 222. The hub 222 supports a ramp 230 that extends from a tool channel of the sheath 200.

Figure 21:
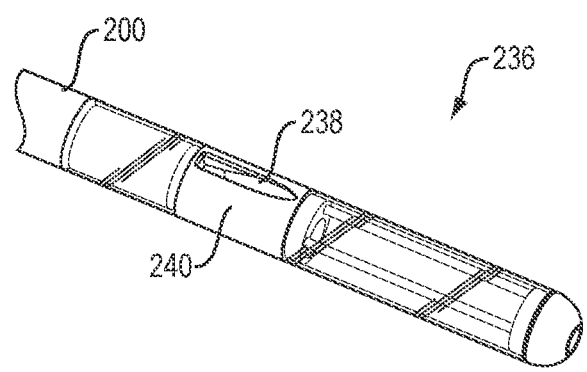
FIG. 21 is an isometric view of the distal end of the elongated access device formed in accordance with one embodiment of the technology described herein.

FIG. 21 shows a distal tip 236 that is similar to the distal tip 204 shown in FIG. 19 except that no ramp device extends from the sheath 200. A ramp feature 238 is formed or machined into a hub 240.

Figure 22:
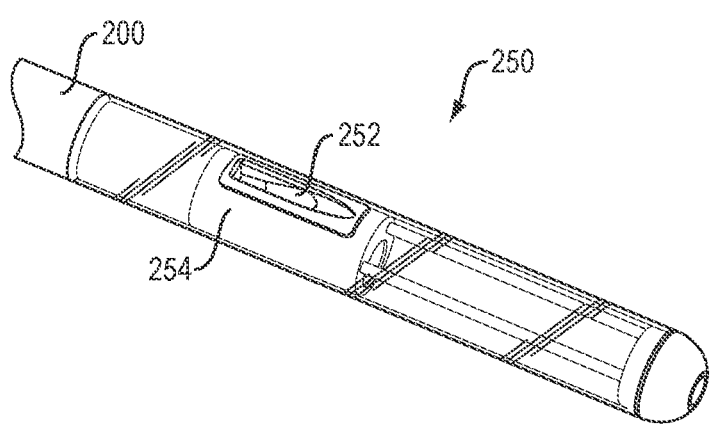
FIG. 22 is an isometric view of the distal end of the elongated access device formed in accordance with one embodiment of the technology described herein.

FIG. 22 shows a distal tip 250 that is similar to the distal tip 220 shown in FIG. 20 except that no ramp device extends from the sheath 200. A ramp feature 252 is formed or machined into a hub 254.

Figure 23:
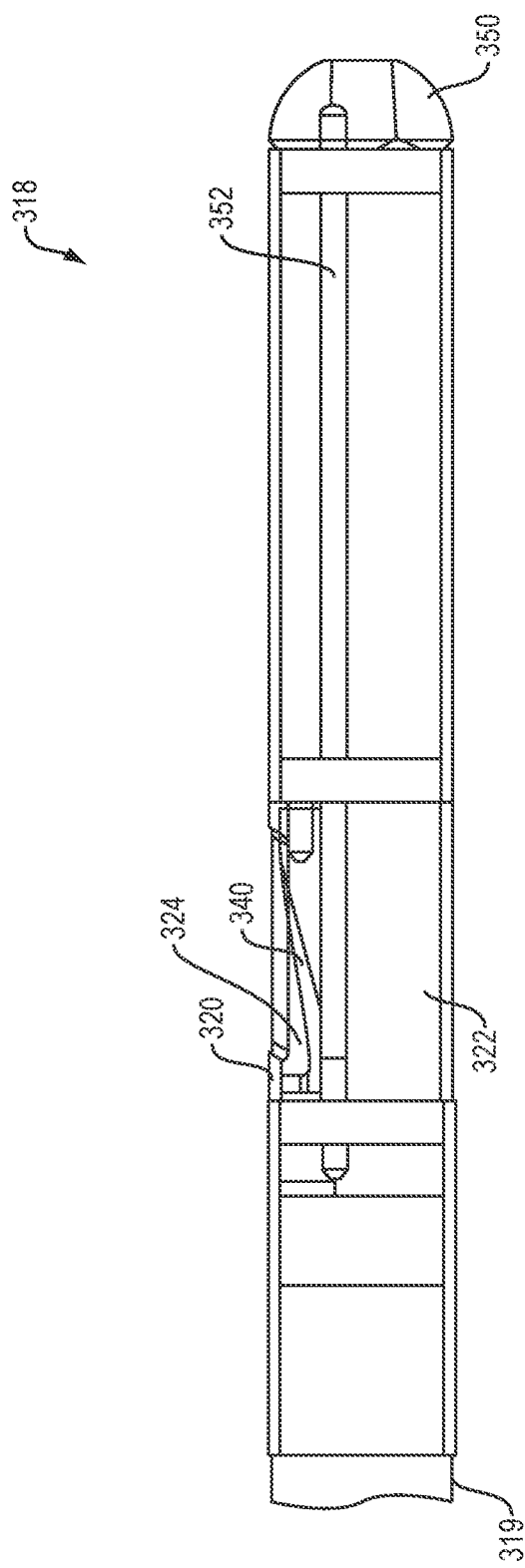
FIG. 23 is a side, partial x-ray view of the distal end of the elongated access device formed in accordance with one embodiment of the technology described herein.
Figure 25:
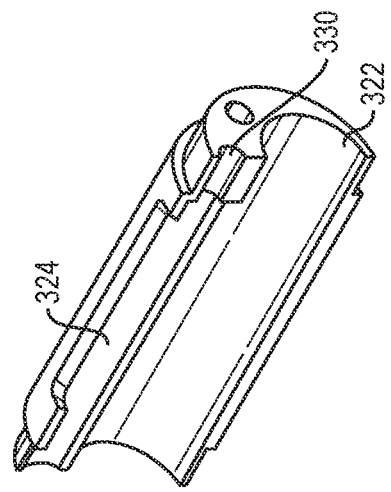
FIG. 25 is an isometric, cross-sectional view of the hub portion shown in FIG. 24.
Figure 27:
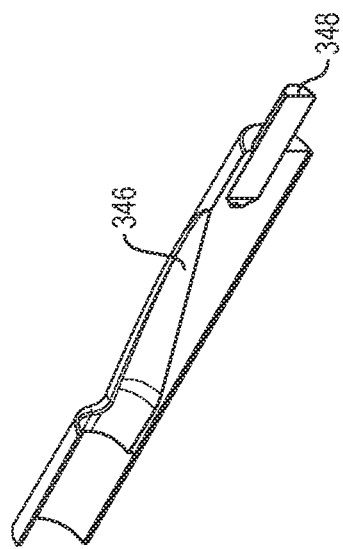
FIG. 27 is an isometric, cross-sectional view of the ramp insert shown in FIG. 26.
Figure 24:
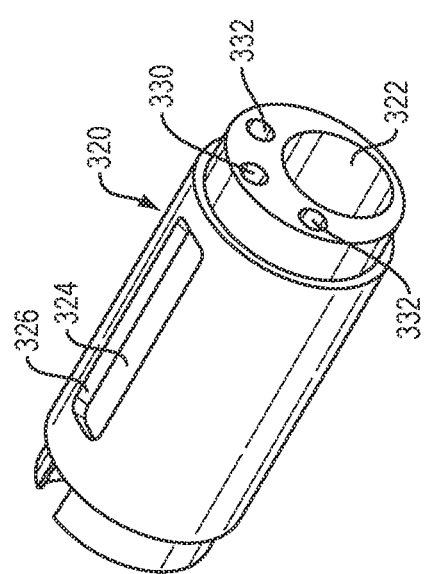
FIG. 24 is an isometric view of a hub portion of the device shown in FIG. 23.
Figure 26:
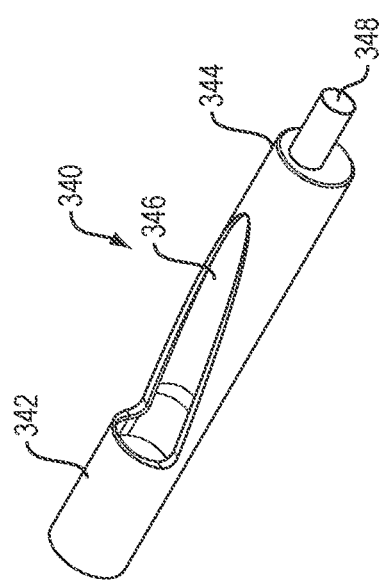
FIG. 26 is an isometric view of a ramp insert of the device shown in FIG. 23.

FIG. 23 shows an x-ray view of an exemplary distal tip 318 that is attached to a sheath 319. The distal tip 318 is similar to the distal tip 120 shown in FIGS. 10-17. The distal tip 318 includes a hub 320, a distal tip 350 and a pair of orientation pins 352. The pins 352 are attached between the distal tip 350 and the hub 320 to define a space for receiving an ultrasound probe. The hub 320 includes a probe lumen 322 and a tool lumen 324 that receives a ramp device 340. As shown in FIGS. 23-27, the ramp device 340 includes a proximal hollow section 342, a distal end 344, a ramp section 346 and a distal protrusion 348. The distal protrusion 348 is either monolithic with the other sections of the ramp device 340 or is a separate piece that is attached within a cavity in the distal section 344 of the ramp device 340.

The hub 320 includes a tool window 326 that is an exit port for the tool lumen 324. The tool lumen 324 distally transitions to a smaller protrusion lumen 330. The ramp device 340 is received within the tool lumen 324 with the distal protrusion 346 being received within the lumen 330.

Figure 28:
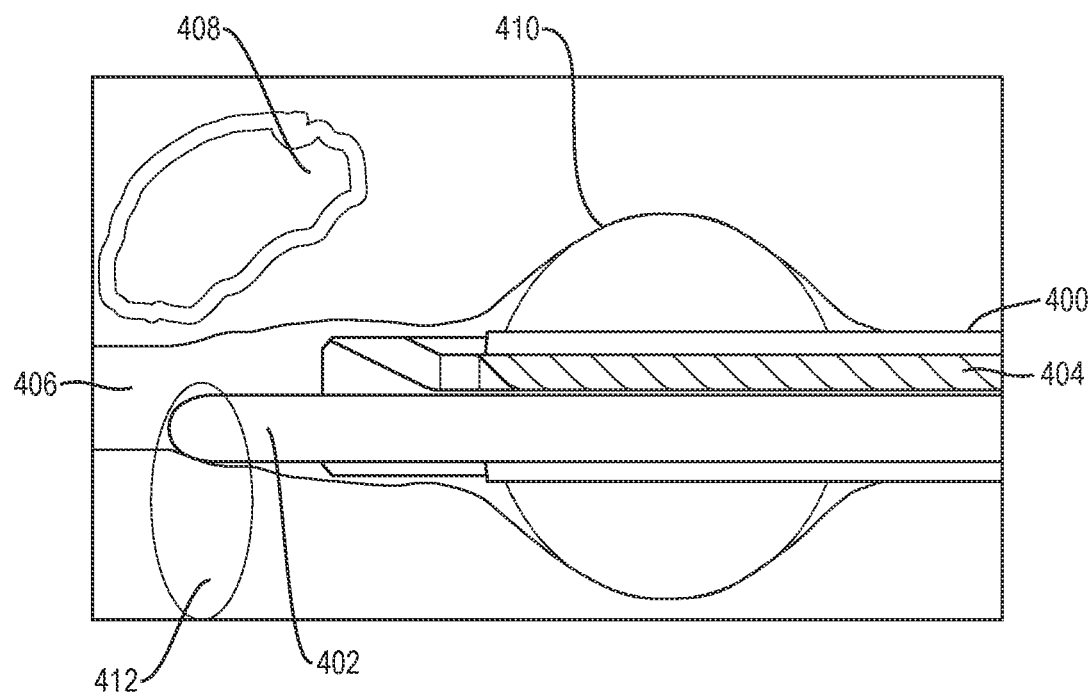
FIG. 28 is a cross-sectional view of a distal end of a dual lumen sheath device in a first mode of operation.
Figure 29:
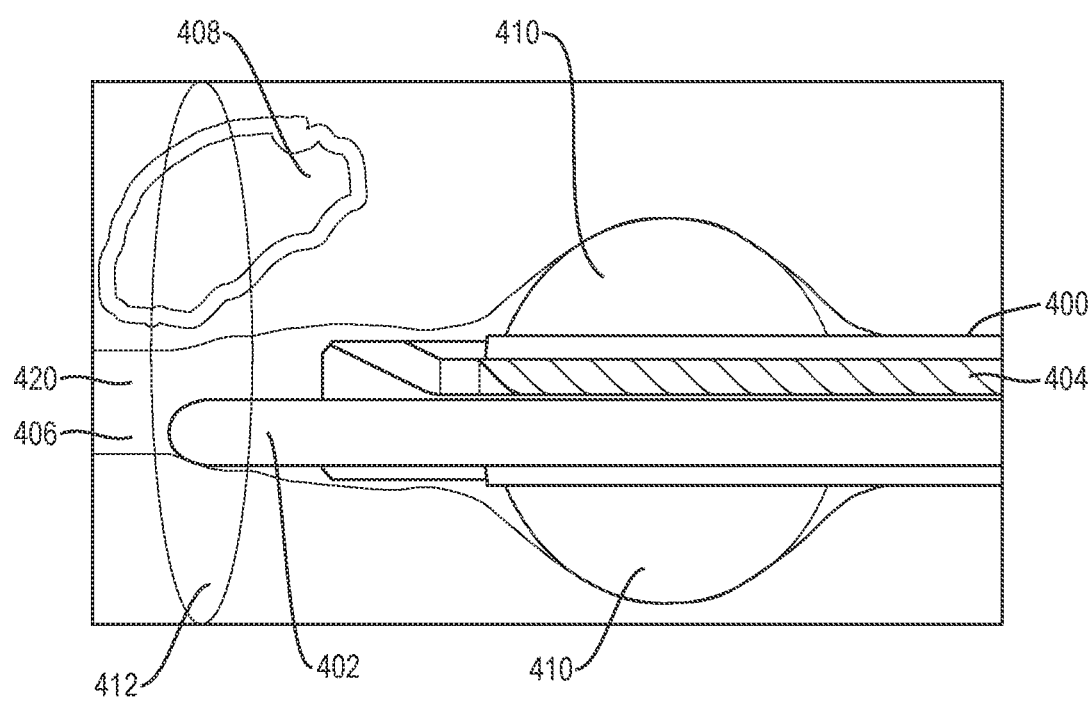
FIG. 29 is a cross-sectional view of the device of FIG. 28 in a second mode of operation.

FIG. 28 illustrates a side, x-ray view of a dual lumen sheath 400 having a first lumen with a ramp at a distal end for slidably housing a needle 404. The dual lumen sheath 400 includes a second lumen that is open at a distal end of the sheath 400. The second lumen slidably receives a radial ultrasound probe 402. A compliant balloon 410 is located outside of the sheath 400 just proximal from a ramp section of the first lumen. A third lumen (not shown) is provided for the balloon 410.

First, after the sheath 400 is advanced into an airway 406 adjacent to a target 408, the balloon 410 is inflated in order to seal off the airway 406. Then, a fluid (e.g., saline) 424 or another material that propagates ultrasound signals is inserted into the airway 406 via the needle 404, the first lumen or the second lumen of the sheath 400. Now the ultrasound probe 402 is advanced past the distal end of the sheath 400. Because the fluid 424 is held within the airway 406 by the blocking balloon 410, ultrasound signals 412 can propagate to the target 408.

A further aspect of the disclosed technology is directed to a method of making an intraluminal tip configured to be attached to a sheath. The method includes forming ramp and nose donuts each of which having first and second plurality of passages by molding or machining. Next, inserting the orientation pins through a plurality of passages. A ramp feature is inserted into a ramp lumen of the ramp donut to stabilize movement of the ramp feature. Then, the tip is attached to a feature of the sheath via the ramp feature. Using a mandrel (not shown), creating an elongated sleeve by forming thermoplastic elastomer material over at least a portion of the respective ramp and nose donuts, the orientation pins, at least a portion of the mandrel and at least a portion of the sheath. Next, inserting the ultrasound probe through one of the first plurality of passage of the ramp donut and injecting the ultrasound gel through one of the second plurality of passages of the nose donut and providing a bottoming out point for the inserted ultrasound probe, which plugs up the one of the second plurality of passages of the nose donut so as to prevent the ultrasound gel from escaping back out.

EMBODIMENTS

A. An elongated access device having respective proximal and distal ends and being used in a medical system, the elongated access device having a medical tool and an ultrasound probe disposed therein, the distal end of the elongated access device includes: a sheath comprising: a first lumen configured to receive the ultrasound probe; a second lumen configured to receive the medical tool; and a lumen liner configured to extend beyond a distal face of the sheath; and a tip configured to be attached to the sheath, the tip comprising: at least one coupling device; a hub comprising: a probe lumen; and a ramp lumen; a nose device; and a ramp device configured to be received within the ramp lumen and configured to receive at least a portion of the lumen liner.

B. The device of A, wherein the ramp device comprises: a proximal end comprising a lumen; a distal end; and a ramp section located between the proximal end and the distal end, the ramp section comprising exit port and a ramp being in fluid communication with the lumen of the proximal end.

C. The device of A or B, wherein the hub comprises: a proximal end; a distal end; and an exit port located between the proximal end and the distal end of the hub adjacent to the ramp lumen.

D. The device of C, wherein the ramp lumen comprises: a first lumen configured to receive the proximal end and the ramp section of the ramp device; and a second lumen configured to receive the distal end of the ramp device.

E. The device of D, wherein the distal end of the ramp device received within the second lumen limits movement of the ramp device relative to the hub.

F. The device of E, wherein the distal end of the ramp device and the second lumen have an oval cross-sectional configuration.

G. The device of any of A-F, wherein the hub comprises: a proximal end having a proximal section and a distal section, the proximal section has an outer diameter that is less than an outer diameter of the distal section; and a distal end having a proximal section and a distal section, the distal section has an outer diameter that is less than an outer diameter of the proximal section.

H. The device of G, wherein the nose device comprises a proximal section, a distal section and a central section located between the proximal and distal sections of the nose device, wherein the proximal section has an outer diameter that is less than an outer diameter of the central section.

I. The device of H, wherein the sheath comprises a proximal section and a distal section, the distal section has an outer diameter that is less than an outer diameter of the proximal section.

J. The device of I, wherein the at least one coupling device comprise a proximal oversleeve and a distal oversleeve, wherein the proximal oversleeve is at least one of adhered, insert molded or thermally bonded to the distal section of the sheath and the proximal section of the proximal end of the hub, wherein the distal oversleeve is at least one of adhered, insert molded or thermally bonded to the distal section of the distal end of the hub and the proximal section of the nose device.

K. The device of any of H-J, wherein the distal section of the nose device is rounded for atraumatic tissue interaction.

L. The device of any of H-K, wherein the nose device comprises a port having a longitudinal axis and configured to receive ultrasound gel.

M. The device of any of H-L, wherein the nose device comprises a proximal surface configured to be compatible with a distal end of the ultrasound probe.

N. The device of any of A-M, wherein the nose device and the at least one oversleeve form a monolithic material.

O. The device of any of A-N, wherein the tip further comprises: one or more orientation pins configured to be engaged with the hub and the nose device, being at least partially encased by the at least one oversleeve.

P. A medical device comprising: a sheath comprising: a first lumen configured to receive an imaging device; a second lumen configured to receive a medical tool; and a lumen liner configured to extend beyond a distal face of the sheath; and a tip configured to be attached to the sheath, the tip comprising: at least one oversleeve; a hub comprising: a proximal end; a distal end; a ramp lumen; an exit port located between the proximal end and the distal end of the hub adjacent to the ramp lumen; and a probe lumen; a nose device; and a ramp device configured to be received within the ramp lumen and configured to receive at least a portion of the lumen liner, the ramp device comprises: a proximal end comprising a lumen; a distal end; and a ramp section located between the proximal end and the distal end of the ramp device, the ramp section comprising an exit port and a ramp being in fluid communication with the lumen of the proximal end.

Q. The medical device of P, wherein the ramp lumen comprises: a first lumen configured to receive the proximal end and the ramp section of the ramp device; and a second lumen configured to receive the distal end of the ramp device and limit movement of the ramp device relative to the hub.

R. The medical device of Q, wherein the distal end of the ramp device and the second lumen have an oval cross-sectional configuration.

S. The medical device of any of P-R, wherein the hub comprises: a proximal end having a proximal section and a distal section, the proximal section has an outer diameter that is less than an outer diameter of the distal section; and a distal end having a proximal section and a distal section, the distal section has an outer diameter that is less than an outer diameter of the proximal section, wherein the nose device comprises a proximal section, a distal section and a central section located between the proximal and distal sections of the nose device, wherein the proximal section of the nose device has an outer diameter that is less than an outer diameter of the central section, wherein the sheath comprises a proximal section and a distal section, the distal section has an outer diameter that is less than an outer diameter of the proximal section, wherein the at least one oversleeve comprise a proximal oversleeve and a distal oversleeve, wherein the proximal oversleeve is at least one of adhered or thermally bonded to the distal section of the sheath and the proximal section of the proximal end of the hub, wherein the distal oversleeve is at least one of adhered or thermally bonded to the distal section of the distal end of the hub and the proximal section of the nose device.

T. The medical device of any of P-S, wherein the tip further comprises: one or more orientation pins configured to be engaged with the hub and the nose device, being at least partially encased by the at least one oversleeve.

While various embodiments of the disclosed technology have been described above, it should be understood that they have been presented by way of example only, and not of limitation. Likewise, the various diagrams may depict an example construction or other configuration for the disclosed technology, which is done to aid in understanding the features and functionality that can be included in the disclosed technology. The disclosed technology is not restricted to the illustrated example construction or configurations, but the desired features can be implemented using a variety of alternative construction and configurations. Indeed, it will be apparent to one of skill in the art how alternative functional, logical or physical partitioning and configurations can be implemented to implement the desired features of the technology disclosed herein. Also, a multitude of different constituent parts names other than those depicted herein can be applied to the various parts. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

What is claimed is:

1. An elongated access device having respective proximal and distal ends and being used in a medical system, the elongated access device having a medical tool and an ultrasound probe disposed therein, the elongated access device comprising:
   a sheath comprising:
      a first lumen configured to receive the ultrasound probe;
      a second lumen configured to receive the medical tool; and
      a lumen liner configured to extend beyond a distal face of the sheath; and
   a tip configured to be attached to the sheath, the tip comprising:
      at least one coupling device;
      a hub comprising:
         a probe lumen; and
         a ramp lumen;

a nose device; and
  a ramp device configured to be received within the ramp lumen and configured to receive at least a portion of the lumen liner.
2. The device of claim 1, wherein the ramp device comprises:
  a proximal end comprising a lumen;
  a distal end; and
  a ramp section located between the proximal end and the distal end, the ramp section comprising an exit port and a ramp being in fluid communication with the lumen of the proximal end.
3. The device of claim 2, wherein the hub comprises:
  a proximal end;
  a distal end; and
  an exit port located between the proximal end and the distal end of the hub adjacent to the ramp lumen.
4. The device of claim 3, wherein the ramp lumen comprises:
  a first lumen configured to receive the proximal end and the ramp section of the ramp device; and
  a second lumen configured to receive the distal end of the ramp device.
5. The device of claim 4, wherein the distal end of the ramp device received within the second lumen limits movement of the ramp device relative to the hub.
6. The device of claim 5, wherein the distal end of the ramp device and the second lumen have an oval cross-sectional configuration.
7. The device of claim 1, wherein the hub comprises:
  a proximal end having a proximal section and a distal section, the proximal section has an outer diameter that is less than an outer diameter of the distal section; and
  a distal end having a proximal section and a distal section, the distal section has an outer diameter that is less than an outer diameter of the proximal section.
8. The device of claim 7, wherein the nose device comprises a proximal section, a distal section and a central section located between the proximal and distal sections of the nose device, wherein the proximal section has an outer diameter that is less than an outer diameter of the central section.
9. The device of claim 8, wherein the sheath comprises a proximal section and a distal section, the distal section has an outer diameter that is less than an outer diameter of the proximal section.
10. The device of claim 9, wherein the at least one coupling device comprises a proximal oversleeve and a distal oversleeve,
  wherein the proximal oversleeve is at least one of adhered, insert molded or thermally bonded to the distal section of the sheath and the proximal section of the proximal end of the hub,
  wherein the distal oversleeve is at least one of adhered, insert molded or thermally bonded to the distal section of the distal end of the hub and the proximal section of the nose device.
11. The device of claim 8, wherein the distal section of the nose device is rounded for atraumatic tissue interaction.
12. The device of claim 8, wherein the nose device comprises a port having a longitudinal axis and configured to receive ultrasound gel.
13. The device of claim 8, wherein the nose device comprises a proximal surface configured to be compatible with a distal end of the ultrasound probe.
14. The device of claim 1, wherein the tip further comprises:
  one or more orientation pins configured to be engaged with the hub and the nose device, being at least partially encased by the at least one coupling device.
15. A medical device comprising:
  a sheath comprising:
    a first lumen configured to receive an imaging device;
    a second lumen configured to receive a medical tool; and
    a lumen liner configured to extend from the second lumen beyond a distal face of the sheath; and
  a tip configured to be attached to the sheath, the tip comprising:
    at least one oversleeve;
    a hub comprising:
      a proximal end;
      a distal end;
      a ramp lumen;
      an exit port located between the proximal end and the distal end of the hub adjacent to the ramp lumen; and
      a probe lumen;
    a nose device; and
    a ramp device configured to be received within the ramp lumen and configured to receive at least a portion of the lumen liner, the ramp device comprises:
      a proximal end comprising a lumen;
      a distal end; and
      a ramp section located between the proximal end and the distal end of the ramp device, the ramp section comprising an exit port and a ramp being in fluid communication with the lumen of the proximal end.
16. The medical device of claim 15, wherein the ramp lumen comprises:
  a first lumen configured to receive the proximal end and the ramp section; and
  a second lumen configured to receive the distal end of the ramp device and limit movement of the ramp device relative to the hub.
17. The medical device of claim 16, wherein the distal end of the ramp device and the second lumen of the ramp lumen have an oval cross-sectional configuration.
18. The medical device of claim 15, wherein the hub comprises:
  a proximal end having a proximal section and a distal section, the proximal section has an outer diameter that is less than an outer diameter of the distal section; and
  a distal end having a proximal section and a distal section, the distal section has an outer diameter that is less than an outer diameter of the proximal section,
  wherein the nose device comprises a proximal section, a distal section and a central section located between the proximal and distal sections of the nose device, wherein the proximal section of the nose device has an outer diameter that is less than an outer diameter of the central section,
  wherein the sheath comprises a proximal section and a distal section, the distal section has an outer diameter that is less than an outer diameter of the proximal section,
  wherein the at least one oversleeve comprise a proximal oversleeve and a distal oversleeve,
  wherein the proximal oversleeve is at least one of adhered or thermally bonded to the distal section of the sheath and the proximal section of the proximal end of the hub, wherein the distal oversleeve is at least one of adhered or thermally bonded to the distal section of the distal end of the hub and the proximal section of the nose device.

19. The medical device of claim 15, wherein the tip further comprises:
one or more orientation pins configured to be engaged with the hub and the nose device, being at least partially encased by the at least one oversleeve.

* * * * *